US00RE41157E

(19) United States
(12) Reissued Patent
Reid et al.

(10) Patent Number: US RE41,157 E
(45) Date of Reissued Patent: Mar. 2, 2010

(54) MICROPARTICLE CARRIERS OF MAXIMAL UPTAKE CAPACITY BY BOTH M CELLS AND NON-M CELLS

(75) Inventors: Robert H. Reid, Kensington, MD (US); John E. VanHamont, Universal City, TX (US); William R. Brown, Denver, CO (US); Edgar C. Boedeker, Placitas, NM (US); Curt Thies, Ballwin, MO (US)

(73) Assignee: The United States of America as represented by the Secretary of the Army, Washington, DC (US)

(21) Appl. No.: 09/451,321

(22) Filed: Nov. 30, 1999

Related U.S. Patent Documents

Reissue of:
(64) Patent No.: 5,693,343
Issued: Dec. 2, 1997
Appl. No.: 08/242,960
Filed: May 16, 1994

U.S. Applications:
(63) Continuation-in-part of application No. 07/867,301, filed on Apr. 10, 1992, now Pat. No. 5,417,986, which is a continuation-in-part of application No. 07/805,721, filed on Nov. 21, 1991, now abandoned, which is a continuation-in-part of application No. 07/690,485, filed on Apr. 24, 1991, now abandoned, which is a continuation-in-part of application No. 07/521,945, filed on May 11, 1990, now abandoned, which is a continuation-in-part of application No. 07/493,597, filed on Mar. 15, 1990, now abandoned, which is a continuation-in-part of application No. 06/590,308, filed on Mar. 16, 1984, now abandoned.

(51) Int. Cl.
*A61K 9/16* (2006.01)
*A61K 9/50* (2006.01)
*A61K 9/14* (2006.01)
*A61K 47/30* (2006.01)

(52) U.S. Cl. ..... 424/491; 424/493; 424/486; 424/497; 424/499; 424/501; 514/788.1; 514/965

(58) Field of Classification Search ..... 424/491, 424/493, 486, 497, 499, 501; 514/788.1, 514/965
See application file for complete search history.

(56) References Cited

U.S. PATENT DOCUMENTS

| | | | | |
|---|---|---|---|---|
| 3,540,444 A | | 11/1970 | Moreland | 128/173 |
| 3,788,315 A | | 1/1974 | Laurens | 128/173 H |
| 4,166,800 A | | 9/1979 | Fong | 252/316 |
| 4,384,975 A | | 5/1983 | Fong | 427/213.36 |
| 4,389,330 A | * | 6/1983 | Tice et al. | 427/213.36 |
| 4,530,840 A | | 7/1985 | Tice et al. | 514/179 |
| 4,542,025 A | | 9/1985 | Tice et al. | 424/78 |
| 4,585,482 A | | 4/1986 | Tice et al. | 106/15.05 |
| 4,622,244 A | | 11/1986 | Lapka et al. | 427/213.32 |
| 4,637,905 A | | 1/1987 | Gardner | 264/4.3 |
| 4,675,189 A | | 6/1987 | Kent et al. | 424/490 |
| 4,798,786 A | | 1/1989 | Tice et al. | 435/177 |
| 4,835,139 A | | 5/1989 | Tice et al. | 514/15 |
| 4,863,735 A | | 9/1989 | Kohn et al. | 524/422 |
| 4,897,268 A | | 1/1990 | Tice et al. | 424/422 |
| 4,938,763 A | | 7/1990 | Dunn et al. | 604/891.1 |
| 4,941,880 A | | 7/1990 | Burns | 604/143 |
| 5,000,886 A | | 3/1991 | Lawter et al. | 264/4.3 |
| 5,019,096 A | | 5/1991 | Fox, Jr. et al. | 623/1 |

(Continued)

FOREIGN PATENT DOCUMENTS

EP 0052510 B2 10/1994

OTHER PUBLICATIONS

Gilding, Biodeggradable polymers for use in surgery–polyglycolic/poly (ac c acid) homo–and copolymers: 1, Polymer, vol. 20, Dec. 1979, pp. 1459–1464.

(Continued)

*Primary Examiner*—Sreeni Padmanabhan
*Assistant Examiner*—Kara R McMillian
(74) *Attorney, Agent, or Firm*—Elizabeth Arwine

(57) ABSTRACT

[In a solvent extraction process for preparing microspheres of a biodegradable polymer, the improvement comprising: preparing a homogenized antigen-sucrose matrix and adding a solvent to the sucrose-antigen matrix to form a solution; preparing a solution of a biodegradable polymer by adding a solvent to the polymer; adding the biodegradable polymer solution to the antigen-sucrose solution; adding an oil to the polymer-sucrose-antigen solution to form an emulsion having a controlled viscosity that corresponds to a predetermined average particle size of distributions of microspheres of biodegradable polymers; centrifuging the emulsion of controlled viscosity and removing the supernatant to obtain microspheres of a predetermined range of particle size distributions of from about 0.5 to about 7.0 micrometers.]

[In immunostimulating composition comprising an encapsulating-microsphere of the biodegradable polymer has an average particle size distribution such that the majority of the microspheres will be taken up by the villous epithelium section of the intestines of a mammalian subject when administered as a vaccine against diseases caused by enteropathogenic organisms.]*A solvent extraction process for preparing microspheres of a biodegradable polymer. The process includes preparing a homogenized antigen-sucrose matrix and adding a solvent to the sucrose-antigen matrix to form a solution. Preparing a solution of a biodegradable polymer by adding a solvent to the polymer. Adding the biodegradable polymer solution to the antigen-sucrose solution. Adding an oil to the polymer-sucrose-antigen solution to form an emulsion having a controlled viscosity that corresponds to a predetermined average particle size of distributions of microspheres of biodegradable polymers. Centrifuging the emulsion of controlled viscosity and removing the supernatant to obtain microspheres of a predetermined range of particle size distributions of from about 0.5 to about 70 micrometers.*

12 Claims, 19 Drawing Sheets

(8 of 19 Drawing Sheet(s) Filed in Color)

U.S. PATENT DOCUMENTS

| | | | | |
|---|---|---|---|---|
| 5,059,187 | A | 10/1991 | Sperry et al. | 604/290 |
| 5,064,413 | A | 11/1991 | McKinnon et al. | 604/70 |
| 5,075,109 | A | 12/1991 | Tice et al. | 424/88 |
| 5,102,872 | A | 4/1992 | Singh et al. | 514/21 |
| 5,129,825 | A | 7/1992 | Discko, Jr. | 433/90 |
| 5,133,701 | A | 7/1992 | Han | 604/289 |
| 5,236,355 | A | 8/1993 | Brizzolara et al. | 433/80 |
| 5,278,202 | A | 1/1994 | Dunn et al. | 523/113 |
| 5,290,494 | A | 3/1994 | Coombes et al. | 264/41 |
| 5,360,610 | A | 11/1994 | Tice et al. | 424/426 |
| 5,384,133 | A | 1/1995 | Boyes et al. | 424/501 |
| 5,407,609 | A | 4/1995 | Tice et al. | 264/46 |
| 5,417,986 | A | 5/1995 | Reid et al. | 424/499 |
| 5,429,822 | A | 7/1995 | Gresser et al. | 424/426 |
| 5,500,228 | A | 3/1996 | Lawter et al. | 424/486 |
| 5,538,739 | A | 7/1996 | Bodmer et al. | 424/501 |
| 5,639,480 | A | 6/1997 | Bodmer et al. | 424/501 |
| 5,643,605 | A | 7/1997 | Cleland et al. | 424/489 |
| 5,648,096 | A | 7/1997 | Gander et al. | 424/489 |
| 5,650,173 | A | 7/1997 | Ramstack et al. | 424/489 |
| 5,688,530 | A | 11/1997 | Bodmer et al. | 424/501 |
| 5,693,343 | A | 12/1997 | Reid et al. | 424/491 |
| 5,762,965 | A | 6/1998 | Burnett et al. | 424/499 |
| 5,811,128 | A | 9/1998 | Tice et al. | 424/501 |
| 5,814,344 | A | 9/1998 | Tice et al. | 424/501 |
| 5,820,883 | A | 10/1998 | Tice et al. | 424/501 |
| 5,853,763 | A | 12/1998 | Tice et al. | 424/489 |

OTHER PUBLICATIONS

Evans, et al. Purification and Characterization of the CFR/I Antigen of Enterotoxigenic Escherichia coli, Infection and Immunity, Aug. 1979, p. 738–748, vol. 25.

Karjalainen, et al., Molecular Cloning and Nucleotide Sequence of the Colonization Factor Antigen I Gene of Escherichia coli, Infection and Immunity, Apr. 1989, p. 1126–1130, vol. 57.

Jeyanthi, et al., Novel, Burst Free Programmable Biodegradable Microspheres For Controlled Release of Polypeptides, Proceedings Int. Symp. control Release Bioact. Mater. (1996) p. 351–352.

Yeh, A novel emulsification–solvent extraction technique for production of protein loaded biodegradable microparticles for vaccine and drug delivery, Journal of Controlled Release, 33 (1005) 437–445.

Yan, Characterization and morphological analysis of protein–loaded poly(lactide–co–glycolide) microparticles prepared by watewr–in–oil–in–water emulsion technique, Journal of Controlled Release, 32 (1994) 231–241.

Wang, et al., Influence of formulation methods on the in vitro controlled release of protein from poly (ester) microspheres Journal of Controlled Release, 17 (1991) 23–32.

Brown, Wonder Drugs' Losing Healing Aura, The Washing Post, Jun. 26, 1995, A section.

Setterstrom, Controlled Release of Antibiotics From biodegradable Microcapsules For Wound infection Control, Chemical Abstracts, 1983, pp. 215–226.

Perez–Casal, et al., Gene Encoding the Major Subunit of CS1 Pili of Human Enterotoxigenic Escherichia Coli, Infection and Immunity, Nov., 1990, pp. 3594–3600, vol. 58, No. 11.

Jordi, et al., Analysis of the first two gnees of the CS1 fimbrial operon in human enterotoxigenic Escherichia coli of serotype 0139:H28, FEMS Microbiology Letters 80, (1991) p. 265–270.

Tan, et al., Mapping the Antigenic Epitopes of Human Dihydrofolate Reductase by Systematic Synthesis of Peptides on solid Supports, The Journal of Biological Chemistry, vol. 265, No. 14, Issue of May 15, pp. 8022–8026 (1990).

McConnel, et al., Antigenic homology within human enterotoxigenic Escherichia coli fimbrial colonization factor antigens: CFA/I, coli–surface–associated antigens (CS)1, CS2, CS4 and CS17, FEMS Microbiology Letters 61 (1989) 105–108.

Van der Zee, Efficient mapping and characterization of a T cell epitope by the simulataneous synthesis of multiple peptides, Eur. J. Immunol. 1989, 19: 43–47.

Cassels, et al., Analysis of Escherichia coli Colonization Factor Antigen I Linear B–Cell Epitopes, as Determined by Primate Responses, following Protein Sequence Verification, Infection and Immunity, Jun. 1992, pp. 2174–2181, vol. 60, No. 6.

Romagnoli, et al. Peptide–MHC Interaction: A Rational Approach to Vaccine Design, Inter, RE, Immunol. 6, 1990, 00 61–73.

Maister, First Oral AIDS Vaccine Trials Near, BioWorld Today, Tuesday, Apr. 19, 1994, p. 4.

Rognan, et al., Molecular Modeling of an Antigenic Complex Between a Viral Peptide and a Class I Major Histocompatibility Glycoprotein, Proteins Structure, Function and Genetics 13 70–85 (1992).

Brown, A hypothetical model of the foreign antigen biinding site of Class II histocompatibility molecules, Nature, vol. 332, Apr. 28, 1988, p. 845–850.

* cited by examiner

* - VISCOSITY ON OIL IN CENTISTOKES @ 40°C

*ONE SECOND EMULSIFICATION WITHOUT AN EMULSION SCREEN

MICROPARTICLE CARRIERS OF MAXIMAL UPTAKE CAPACITY BY BOTH M CELLS AND NON-M CELLS

Matter enclosed in heavy brackets [ ] appears in the original patent but forms no part of this reissue specification; matter printed in italics indicates the additions made by reissue.

I. CROSS REFERENCE

This application is a continuation-in-part of U.S. patent application Ser. No. 07/867,301 filed Apr. 10, 1992, now U.S. Pat. No. 5,417,986, which in turn is a continuation-in-part of U.S. patent application Ser. No. 07/805,721, filed Nov. 21, 1991, now abandoned, which in turn is a continuation-in-part of U.S. patent application Ser. No. 07/690,485 filed Apr. 24, 1991, now abandoned, which in turn is a continuation-in-part of U.S. patent application Ser. No. 07/521,945 filed May 11, 1990, now abandoned, which in turn is a continuation-in-part of U.S. patent application Ser. No. 07/493,597 filed Mar. 15, 1990, now abandoned, which in turn is a continuation-in-part of U.S. patent application Ser. No. 06/590,308 filed Mar. 16, 1984, pending.

II. GOVERNMENT INTEREST

The invention described herein may be manufactured, licensed and used by or for governmental purposes without the payment of any royalties to us thereon.

The file of this patent contains at least one drawing executed in color. Copies of this patent with color drawing (s) will be provided by the Patent and Trademark Office upon request and payment of the necessary fee.

III. FIELD OF THE INVENTION

The invention pertains in part to a method for preparing particle size distributions of microparticles of biodegradable polymers having the capacity to be maximally absorbed in both M cells and non-M cells in the Peyer's patches (PP) follicle-associated epithelium (FAE) and the villous epithelium region so that when the microparticles are used as carries of immunogens for oral immunization, the maximal conditions for uptake by gut lymphoid tissues will absorb any antigens so as to induce production of antibodies against diseases caused by the antigen or other enteropathogenic organisms, when using antigens encapsulated within biodegradable-biocompatible microspheres prepared by the process of the invention.

IV. BACKGROUND OF THE INVENTION

Infectious agents generally have their first contact with host organisms at a mucosal surface. Therefore, mucosal protective immune mechanisms are of key importance in preventing these agents form colonizing or penetrating the mucosal surface. It is apparent from past studies that a protective mucosal immune response can best be obtained by introduction of the antigen at the mucosal surface; however, parenteral immunization has not been an effective method to induce mucosal immunity. Antigen taken up by the gut-associated lymphoid tissue (GALT), primarily by the Peyer's patches stimulates T helper cells ($T_H$) to assist in IgA B cell responses or stimulates T suppressor cells ($T_{KS}$) to mediate the unresponsiveness of oral tolerance.

While particulate antigen appears to shift the responses towards the ($T_H$), soluble antigens favor a response by the ($T_{KS}$).

Although studies have demonstrated that oral immunization does induce an intestinal mucosal immune response, large doses of antigen are generally required to achieve sufficient local concentrations in the Peyer's patches. Further, unprotected protein antigens tend to be degraded or they complex with secretory IgA in the intestinal lumen.

One approach to overcoming the aforementioned problems is to homogeneously disperse the antigen of interest within the polymeric matrix of biodegradable, biocompatible microspheres that are specifically taken up by GALT. Eldridge, et al.[1] have used a murine model to show that orally-administered 1–10 micrometer microspheres consisting of polymerized lactide and glycolide, (the same materials used in resorbable sutures), were readily taken up into Peyer's patches, and that 1–5 micrometer sizes were rapidly phagocytized by macrophages. Microspheres that were 5–10 micrometers (microns) remained in the Peyer's patches for up to 35 days, whereas those less than 5 micrometer disseminated to the mesenteric lymph node (MLN) and spleen within migrating MAC-$1^+$ cells.

[1]Biodegradable Microspheres: Vaccine Delivery System For Oral Immunization, 1989, 146.

However, Eldridge, et al. used 50 μm microspheres of poly (DL-lactide-co-glycolide) composed of molar parts of polymerized lactide and glycolide (85:15 DL-PLG), which biodegrades to completion in approximately 24 weeks after intramascular injection.

Poly (DL-lactide-co-glycolide) composed of equal molar parts of polymerized lactide and glycolide (50:50 DL-PLG) is the more stable or lest biodegradable, and biodegrades to completion after 25 weeks.

Therefore, there is a need extant in the biodegradable microsphere field to provide a method of producing poly (DL-lactide-co-glycolide) materials of 50:50 DL-PLG that is more biodegradable and capable of being taken up by both M cells and non-M cells in the Peyer's patches follicle-associated epithelium when used as microencapsulant as carriers for antigens for enteric immunization.

V. SUMMARY OF THE INVENTION

One object of the invention is to provide a method for producing microparticles of biodegradable-biocompatible microspheres having an average particle size distribution that maximizes uptake of the microspheres by both M cells and non-M cells, either in the villous epithelium or in the Peyer's patches, follicle-associated epithelium so that, upon encapsulating antigens or other chemotherapeutic agents within these microspheres, large doses of antigen will not be required to achieve sufficient local concentrations in these regions of the intestines when these microparticles are used as carriers of immunogens for oral or other types of immunization.

A further object of the invention is to provide a method for producing microspheres composed of poly (DL-lactide-co-glycolide) having an average particle size distribution so as to maximize the uptake of these microspheres into the lymphoid tissue of the gut through uptake by both M cells and non-M cells, either in the villous epithelium or in the PP follicle-associated epithelium, in order to enable smaller doses of antigen to achieve sufficient local concentrations in these regions of the intestines when using the poly (DL-lactide-co-glycolide) as a carrier of immunogens for oral or other types of immunization.

A yet further object of the invention is to provide a method for producing an average distribution of particle sizes of the most stable or least biodegradable poly (DL-lactide-co-glycolide) having equal molar parts of polymerized lactide and glycolide (50:50 DL-PLG) so as to maximize uptake or microspheres of this copolymer by both M cells and non-M cells, either in the villous epithelium or in the PP follicle-associated epithelium when using this copolymer as a carrier of immunogens for oral or other types of immunization in mammals.

In general the invention is accomplished by modifying the solvent extraction process for producing microspheres so that the average particle size distribution can be controlled by altering the viscosity of the emulsion, either by: 1) predilution of the emulsion oil with extractant solvent; 2) adding thickening agents such as polybutylene to the emulsion oil to deliberately increase its viscosity; 3) use of oils with predefined viscosities for preparation of the emulsion; or 4) by deliberately adjusting the viscosity of paraffin oil used by preheating it to a temperature which yields the desired viscosity. When the emulsion time is kept sufficiently short to prevent a significant temperature increase during the emulsification process, the oil viscosity is the primary process parameter in determining the average distribution of particle size ranges of the spheres' diameter. Variations in screen and rotor dimensions of the equipment and emulsification speed and time have negligible effects on the outcome of the microspheres diameter.

VI. BRIEF DESCRIPTION OF THE DRAWINGS

Figure 1:
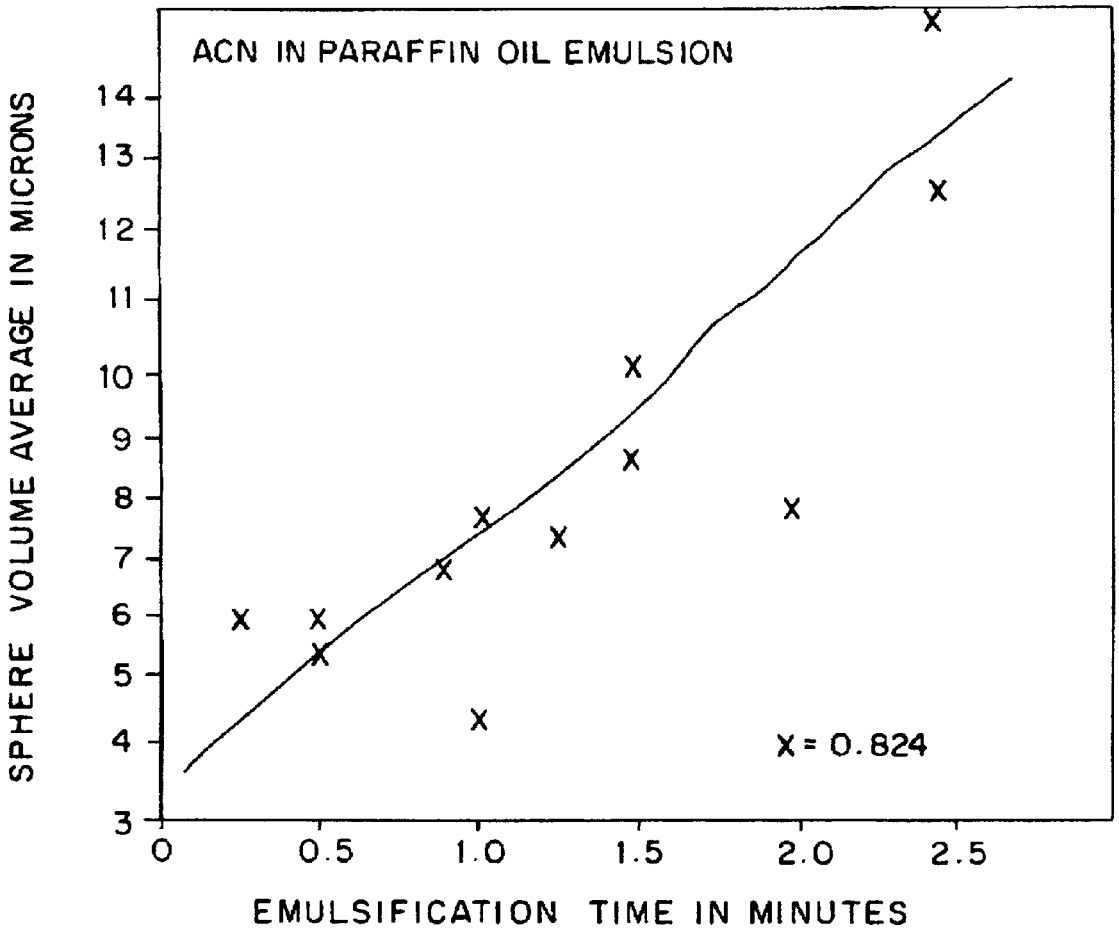
FIG. 1 shows that, during preparation of the microspheres, the spheres actually got larger as the emulsion time was increased.
Figure 2:
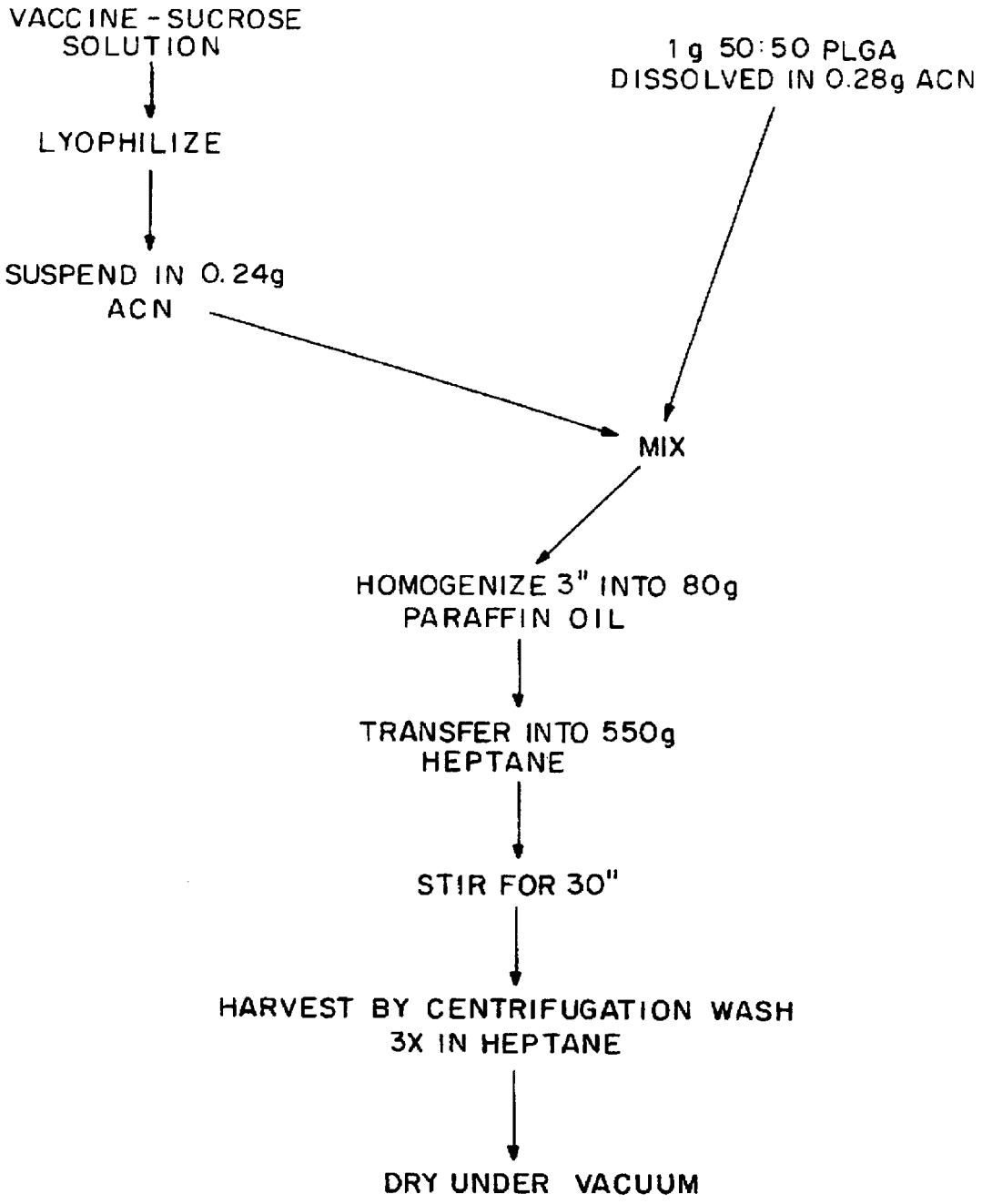
FIG. 2 is a schematic showing the preparation of sucrose-loaded vaccine placebo microspheres.
Figure 3:
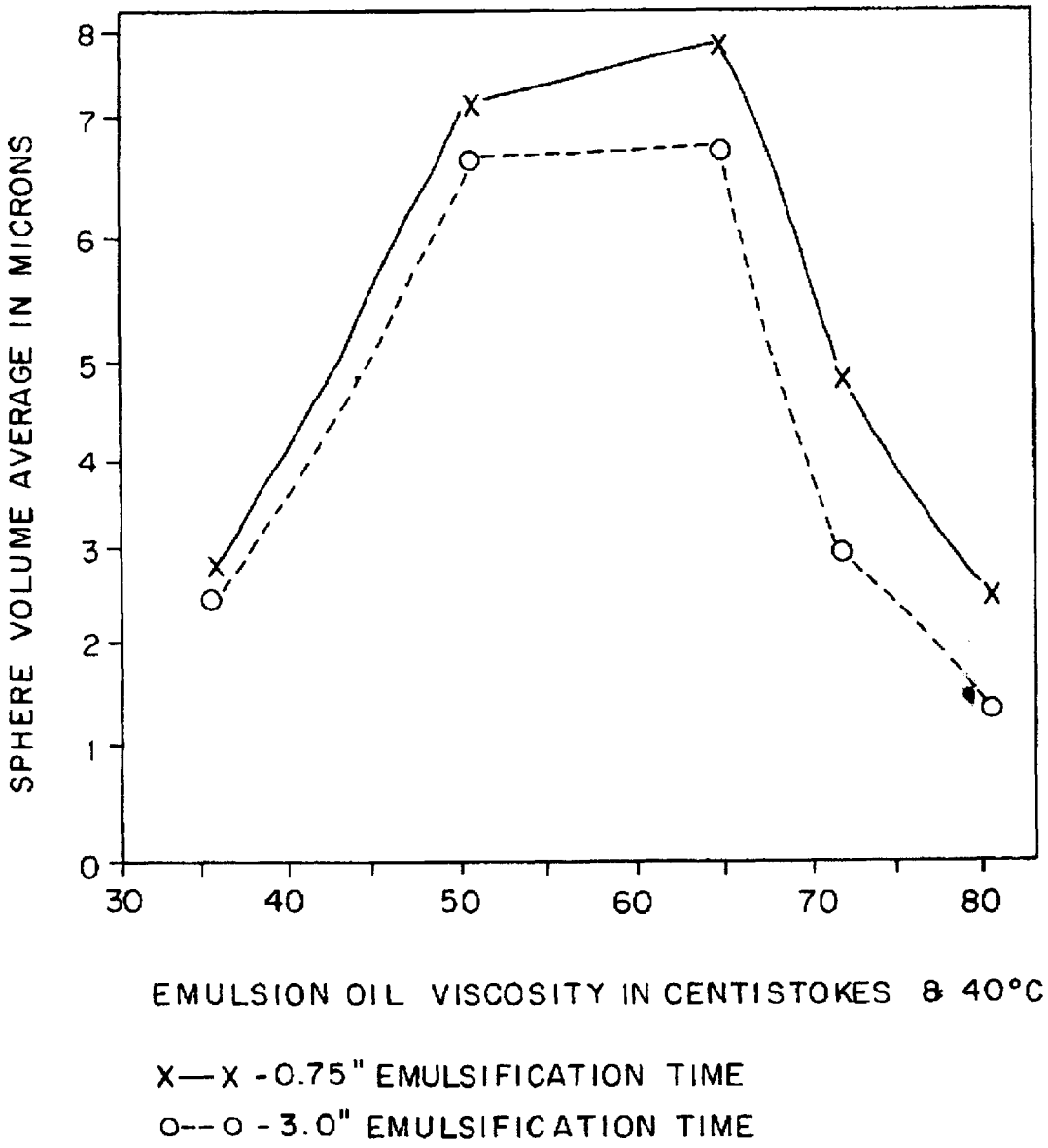
FIG. 3 is a graph showing substitution of stable-viscosity machine oils or paraffin oils during the formation of the emulsion to accomplish sphere populations whose average sizes and volumes decreased with increasing emulsification times, in contrast to that which was observed for emulsions formed with paraffin oil as shown in FIG. 1.
Figure 4:
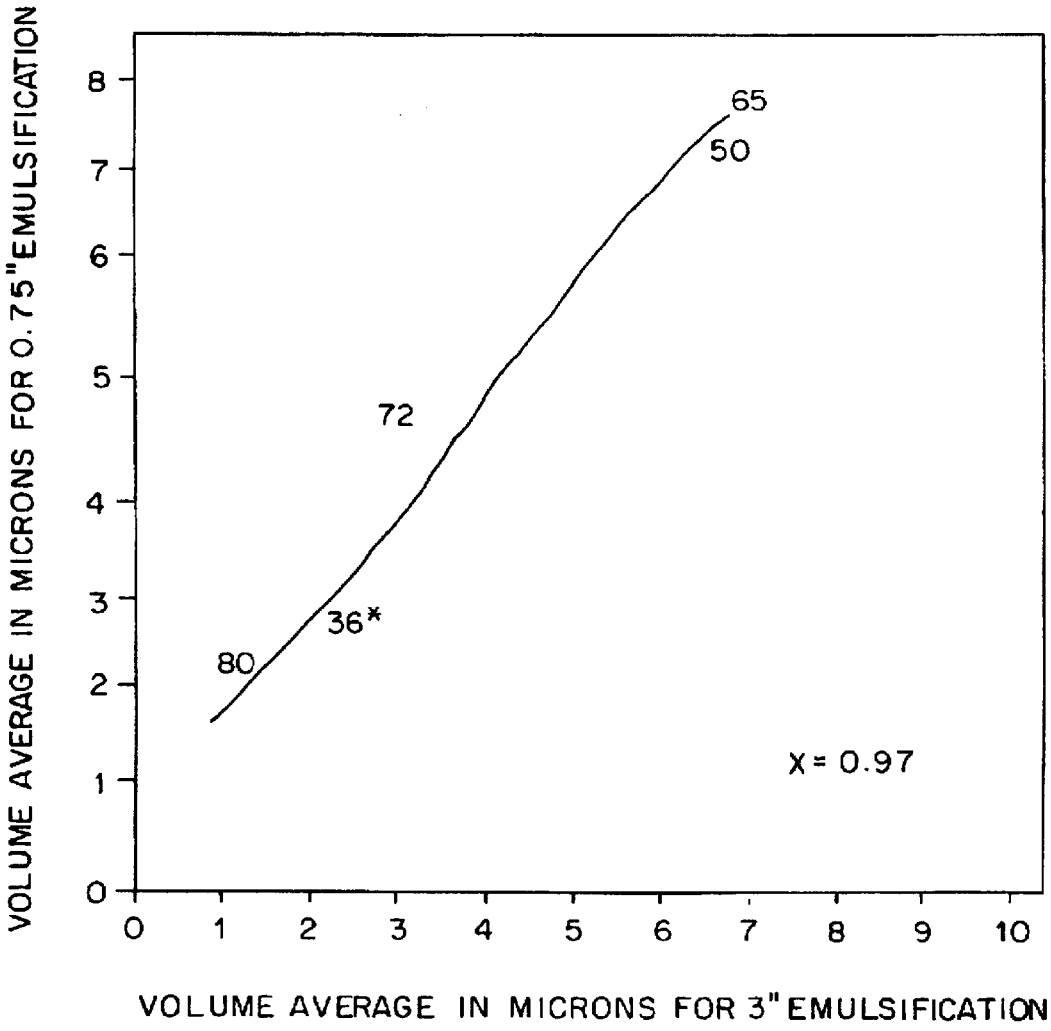
FIG. 4 shows the consistent relationship between sphere sizes at 3.0 minutes versus 0.75 minutes across all viscosities of oil tested, and show that sphere sizes are directly related to viscosity.
Figure 5:
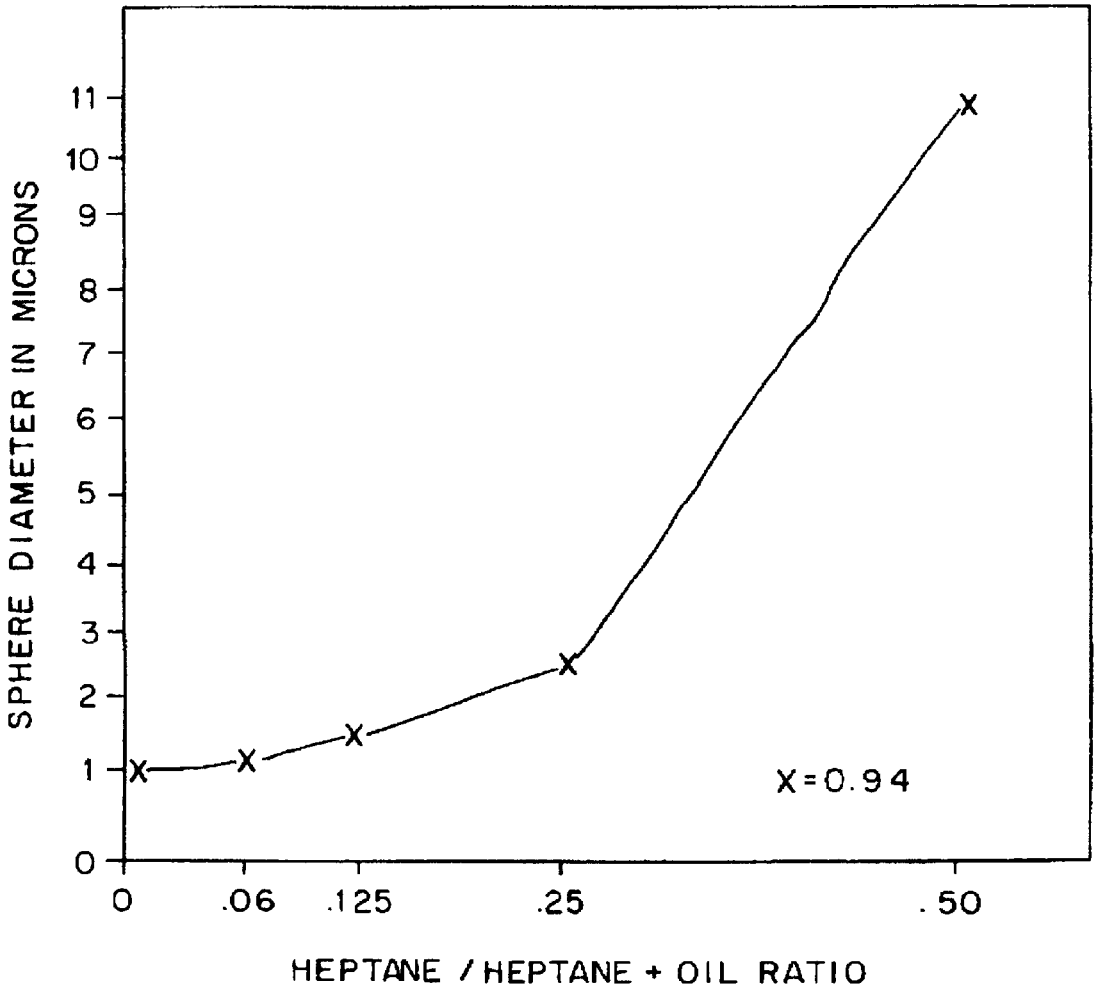
FIG. 5 shows the reducing the viscosity of the paraffin oil by diluting it with heptane resulted in the formation of progressively larger spheres.
Figure 6:
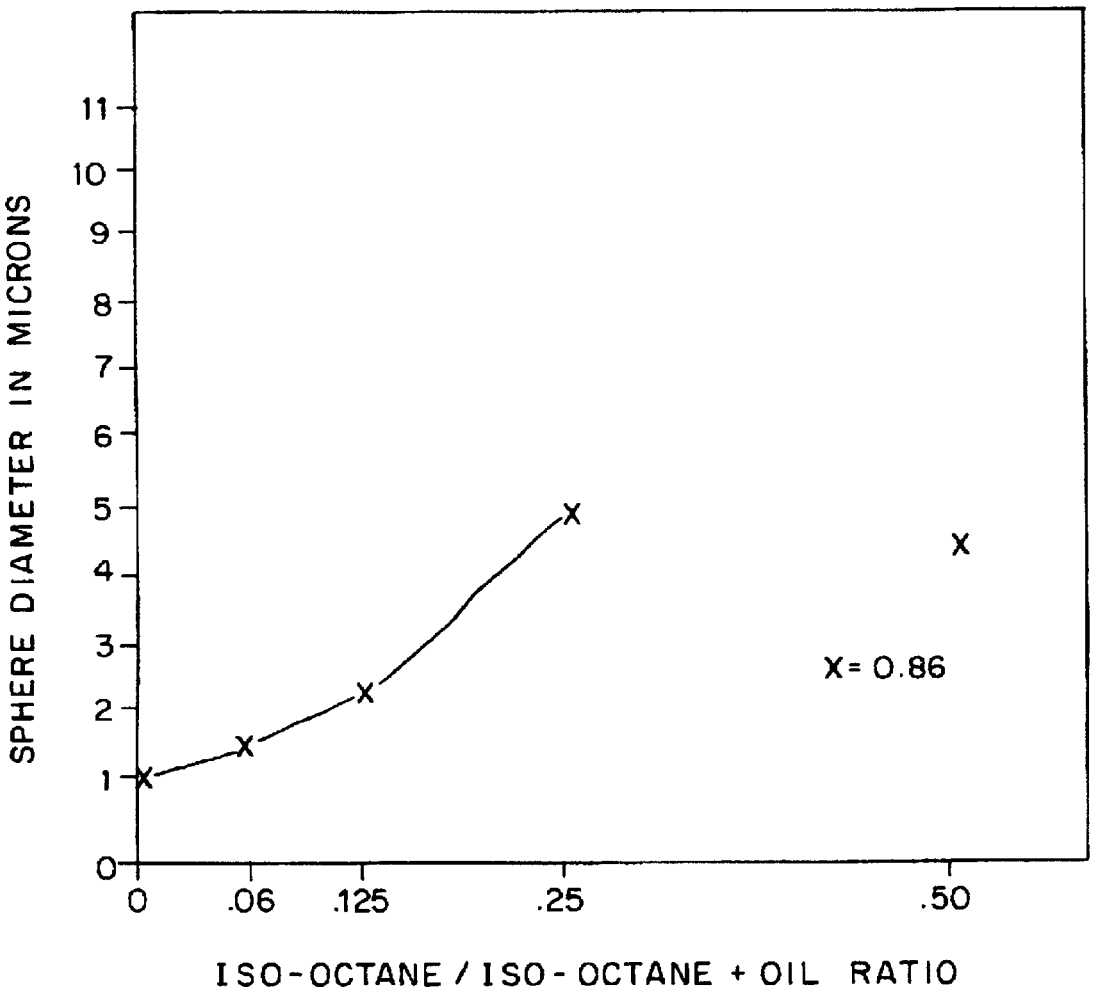
FIG. 6 shows the reducing the viscosity of the paraffin oil by diluting it with iso-octane resulted in the formation of progressively larger spheres.
Figure 7:
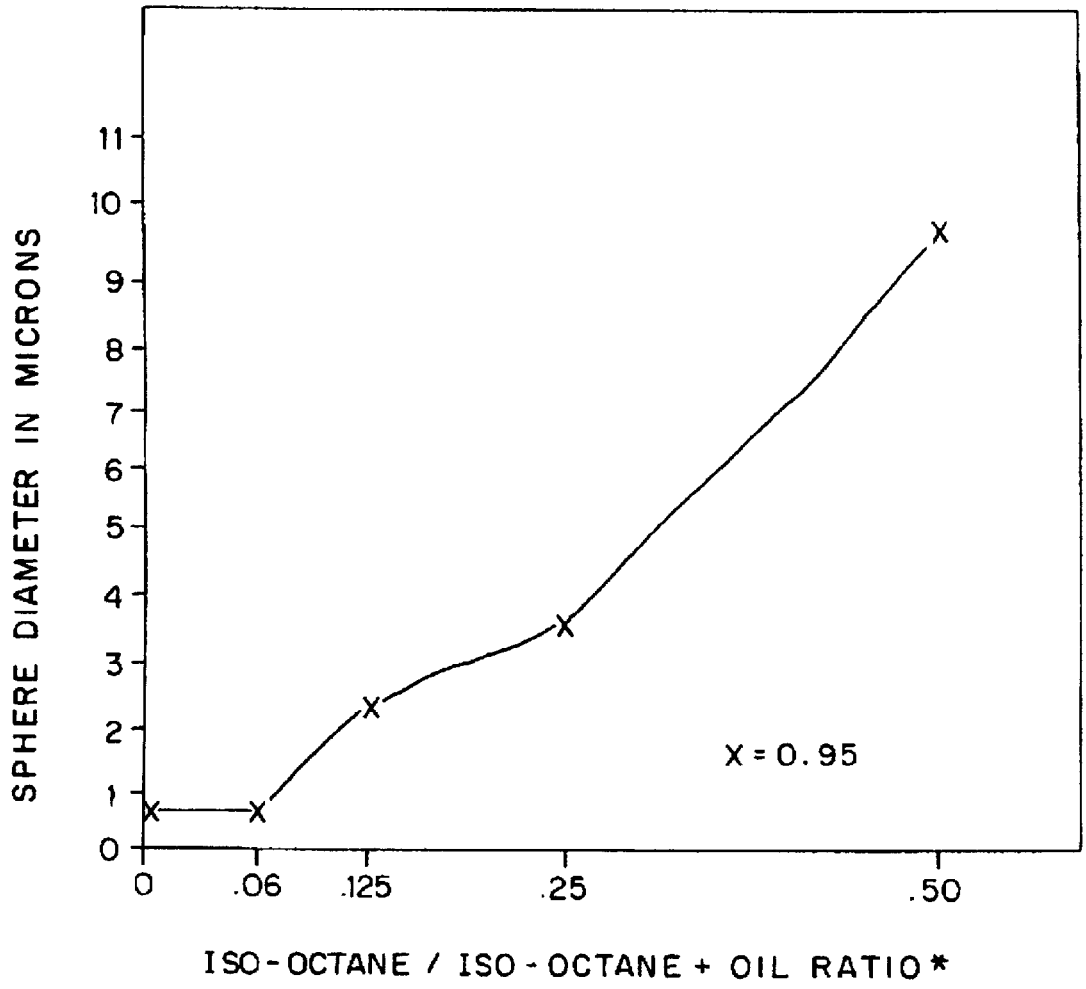
FIG. 7 shows that when reducing the viscosity of the paraffin oil by diluting it with heptane using one second emulsification without an emulsion screen, resulted in the formation of progressively larger spheres.
Figure 8:
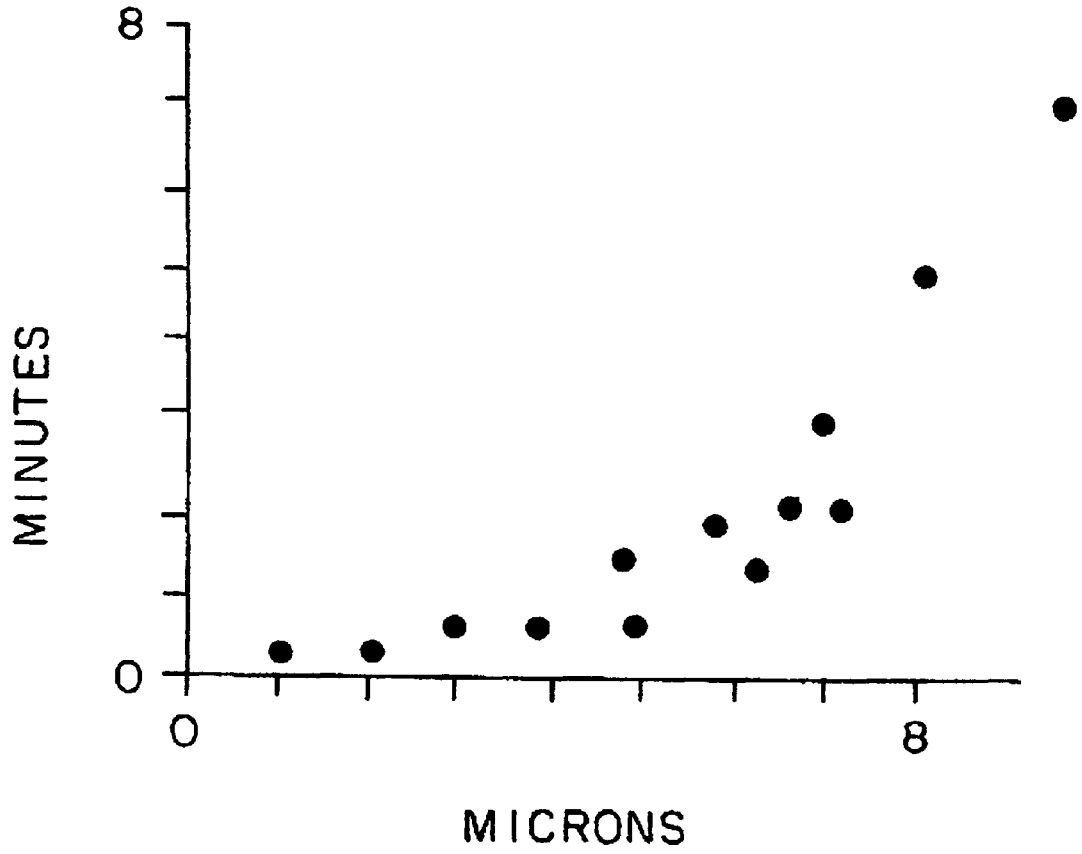
FIG. 8 shows microsphere volume average versus emulsification time in paraffin oil.
Figure 9:
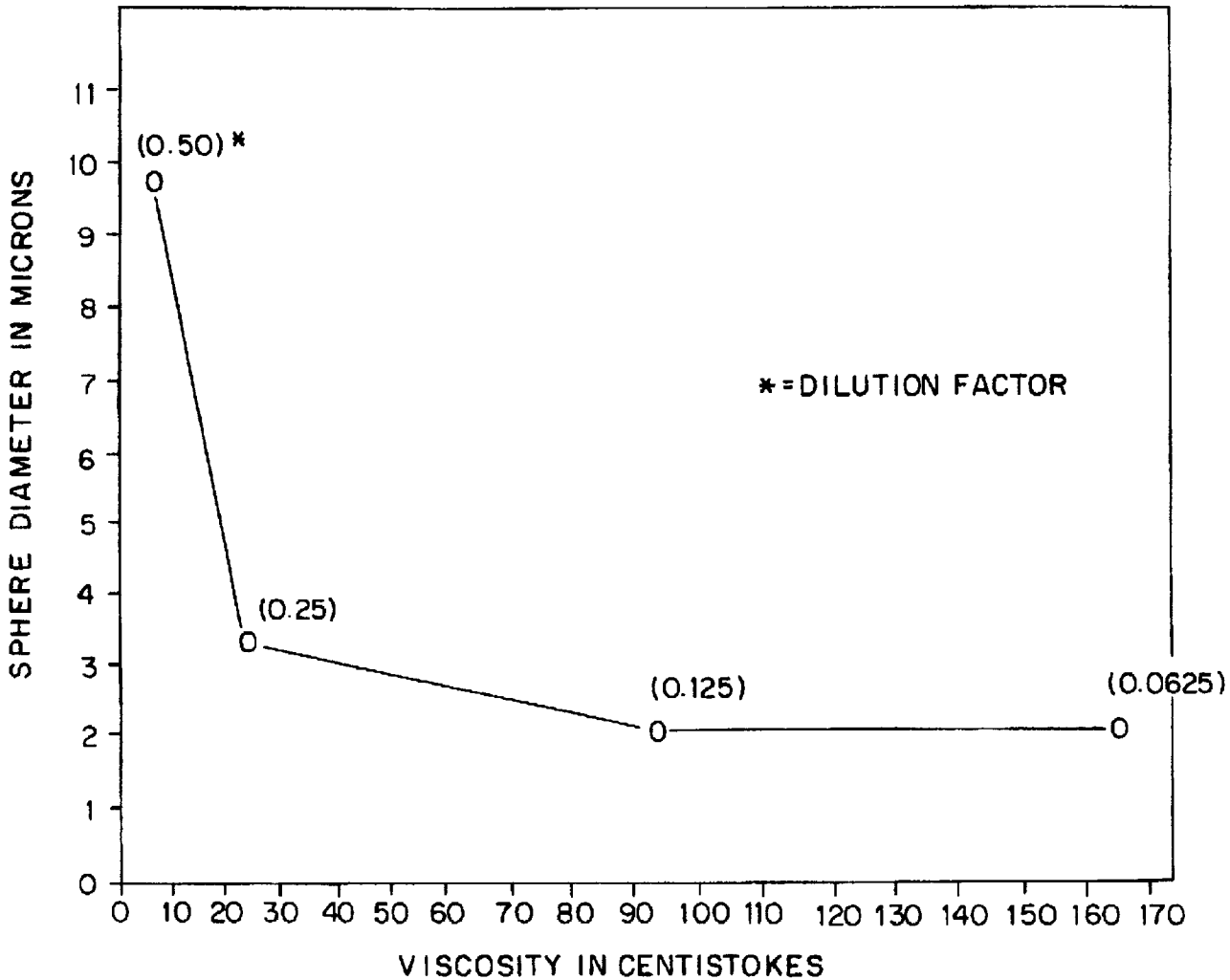
FIG. 9 shows viscosity versus sphere diameter obtained with paraffin oil diluted with iso-octane.
Figure 10:
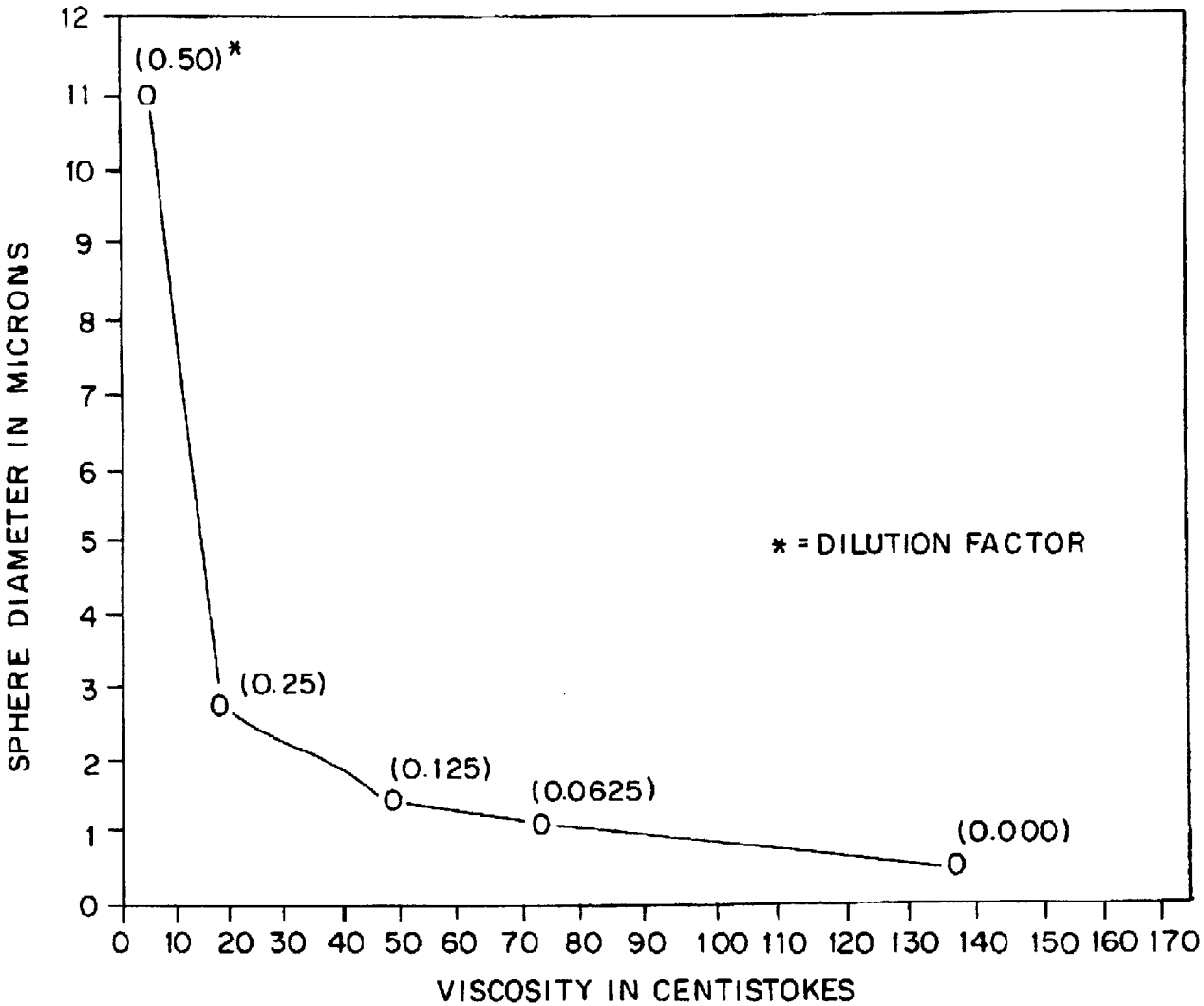
FIG. 10 shows viscosity versus sphere diameter obtained with paraffin oil diluted with heptane.
Figure 11:
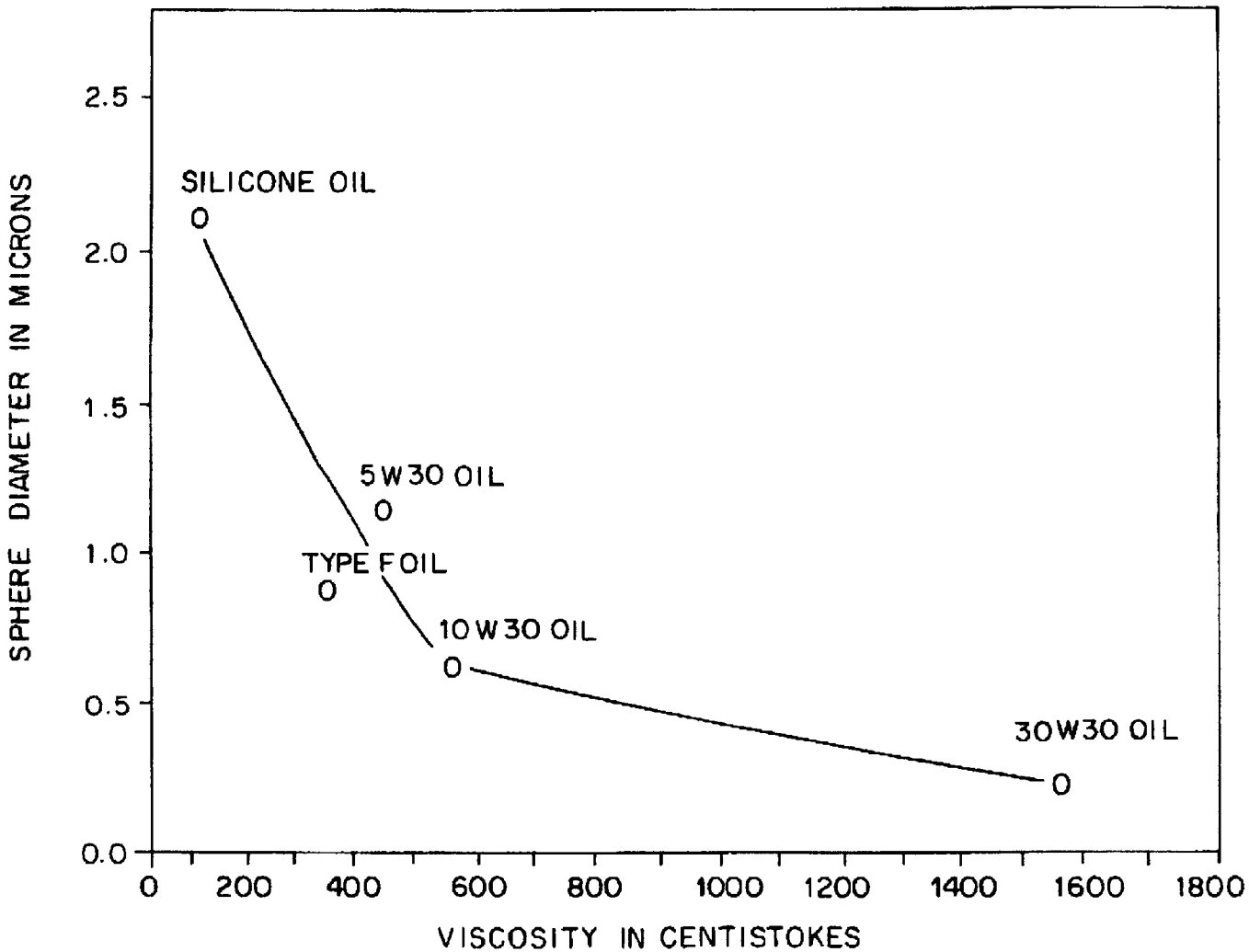
FIG. 11 shows viscosity versus sphere diameter obtained with machine oils.
Figure 12:
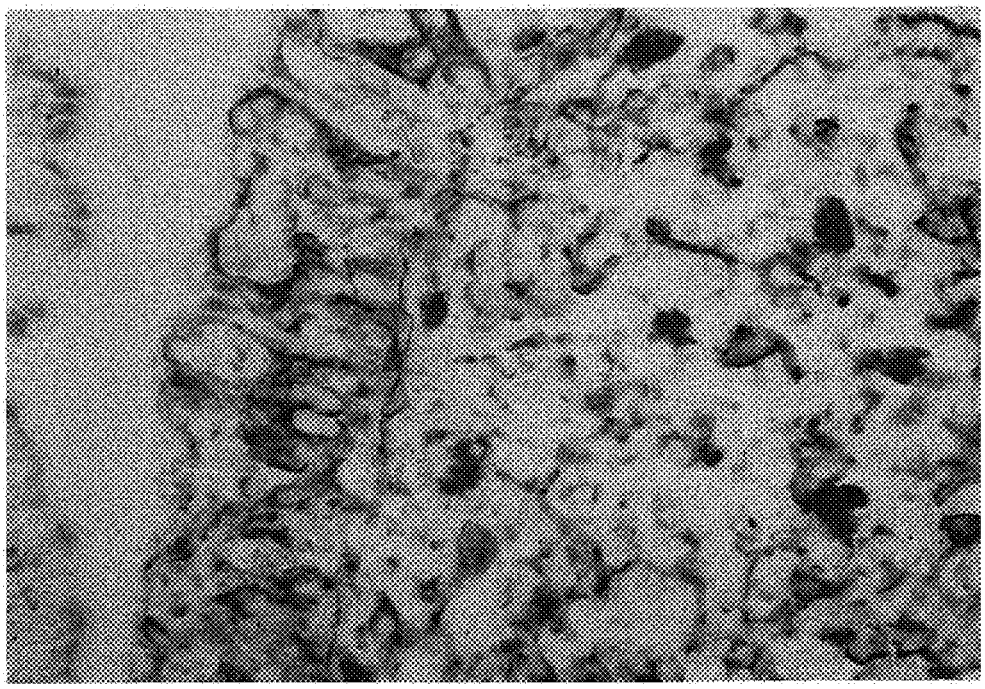
FIG. 12 is a color photograph of the flank region of the intestinal lymphoid follicle of a New Zealand white rabbit histochemically stained for acid phosphatase (red) and immunohistochemically stained for the MHCII antigen.
Figure 13:
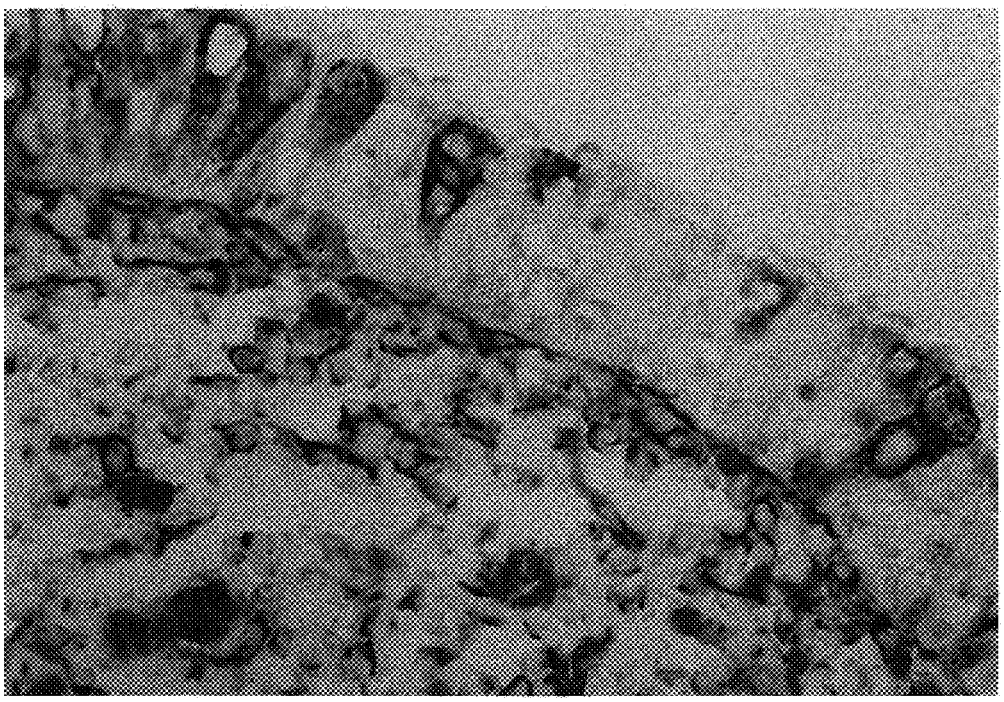
FIG. 13 is a color photograph of the flank region of the intestinal lymphoid follicle histochemically stained for alkaline phosphasate (red) and immunohistochemically stained for the MHCII antigen.
Figure 14:
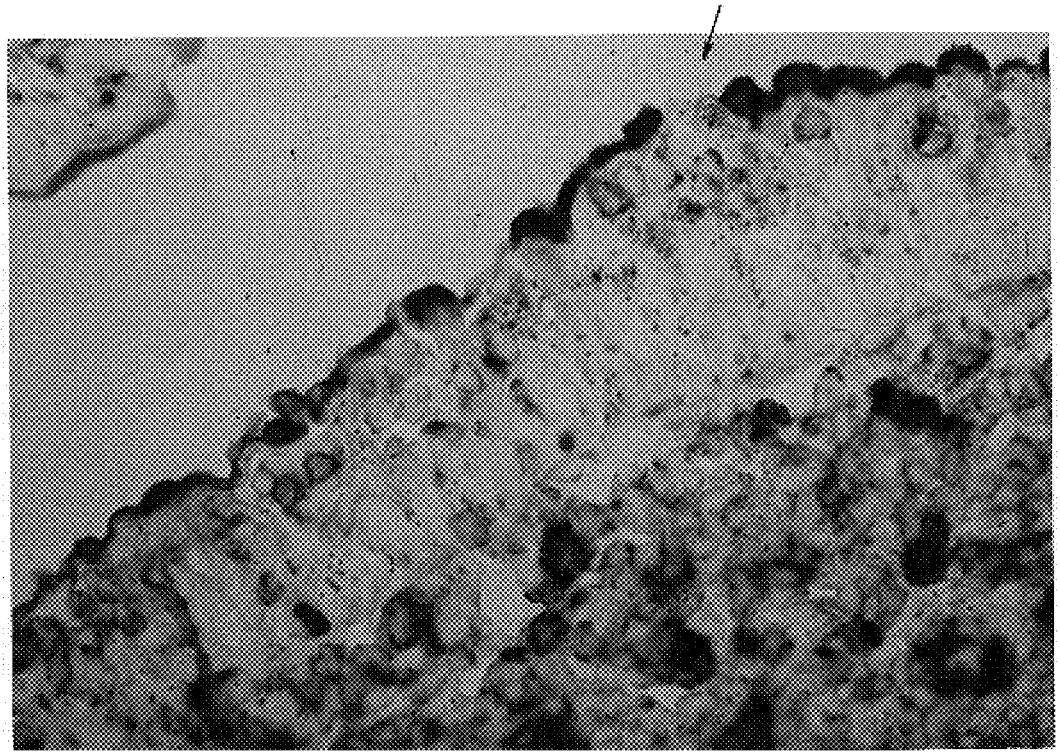

FIG. 14 is a color photograph of the flank region of the intestinal lymphoid follicle of a New Zealand white rabbit showing numerous microspheres of the poly (DL-lactide-co-glycolide) composed of molar parts of polymerized lactide and glycolide (50:50 DL-PLG) in the company of MHCII-positive cells in lymphoid pockets in the Follicle Associated Epithelium (FAE), and wherein some of the microsphere particles are within the cells (arrows). In the lymphoid follicle, numerous MHUCII-positive cells are present, and some have microspheres associated with them (arrowheads).

Figure 15:
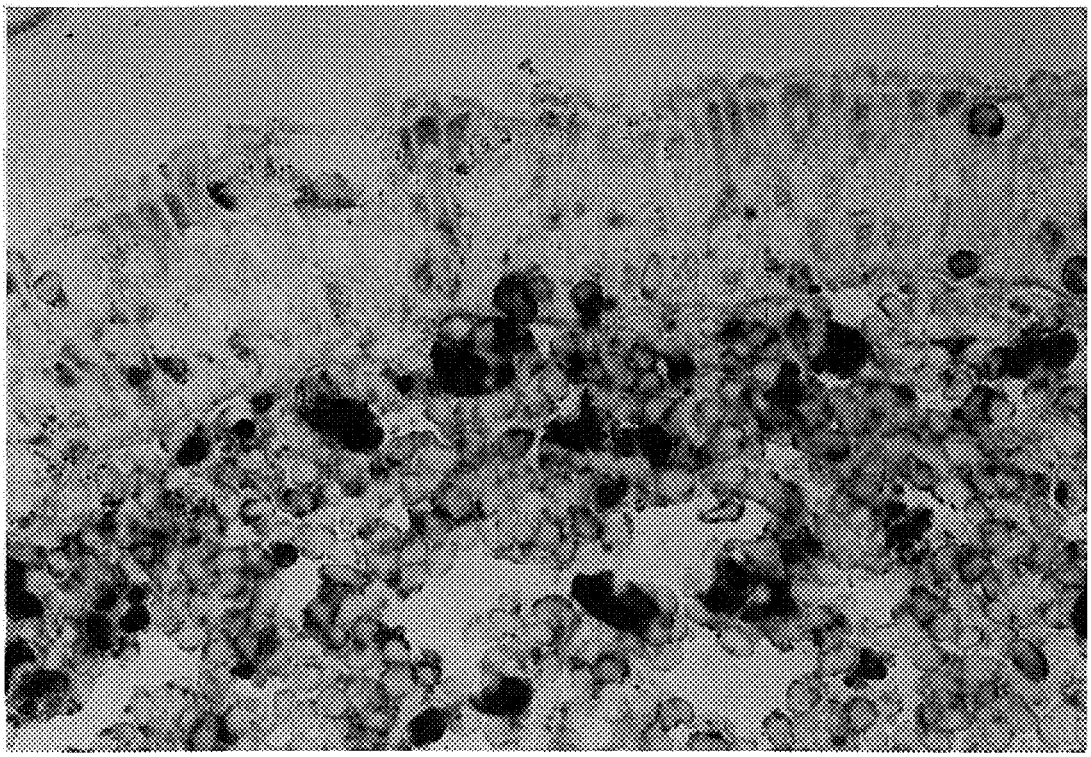

FIG. 15 is a color photograph showing that both kinds of particles were taken up by the follicle-associated epithelium and entered the underlying lymphoid tissues of Peyer's patches (fluoresceinated microspheres are more easily visualized, and as a consequence they are shown in the photograph).

Figure 16:
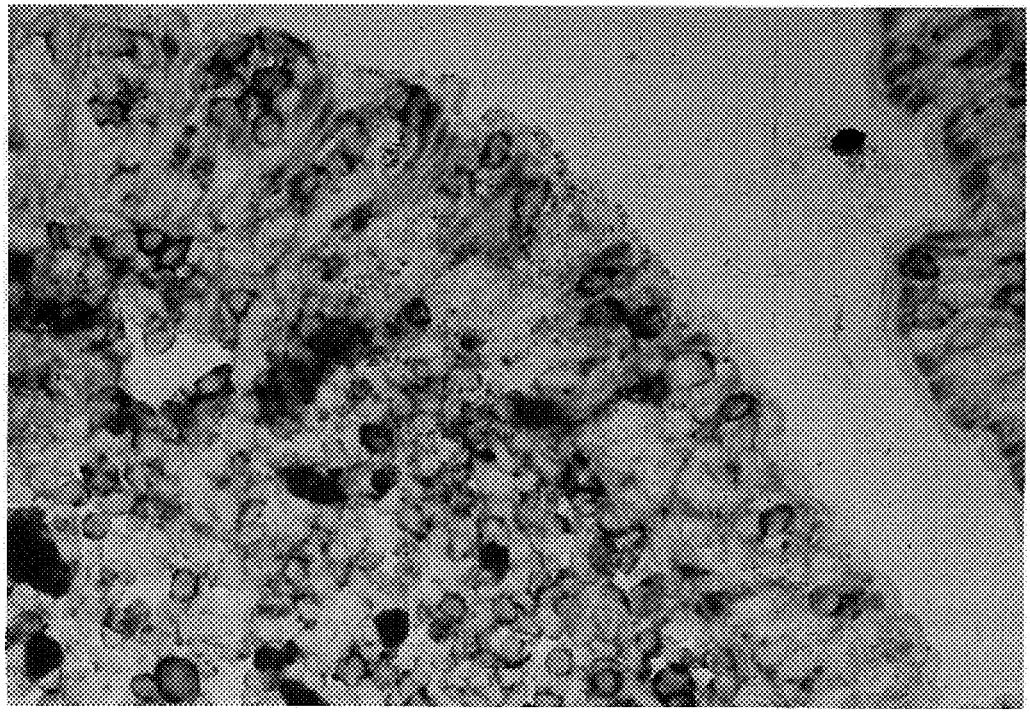

FIG. 16 is a color photograph showing the flank region of the previously illustrated intestinal lymphoid follicle and the adjacent villous stained for acid phosphotates (red) and CD43 (pan-T cell). Numerous CD43-positive cells are present in the FAE and in the lymphoid follicle. Microparticles in the FAE are in the company of CD43-positive cells in the lymphoid pockets, and some of the particles are within the cells (arrows). The CD43 cells are CD8- and CD4-negative, and Igu-positive cells are sparse in the FAE. The microparticles have not entered the epithelium of the villous (v) adjacent to the lymphoid follicle, although some are present nearby in the lumen.

Figure 17:
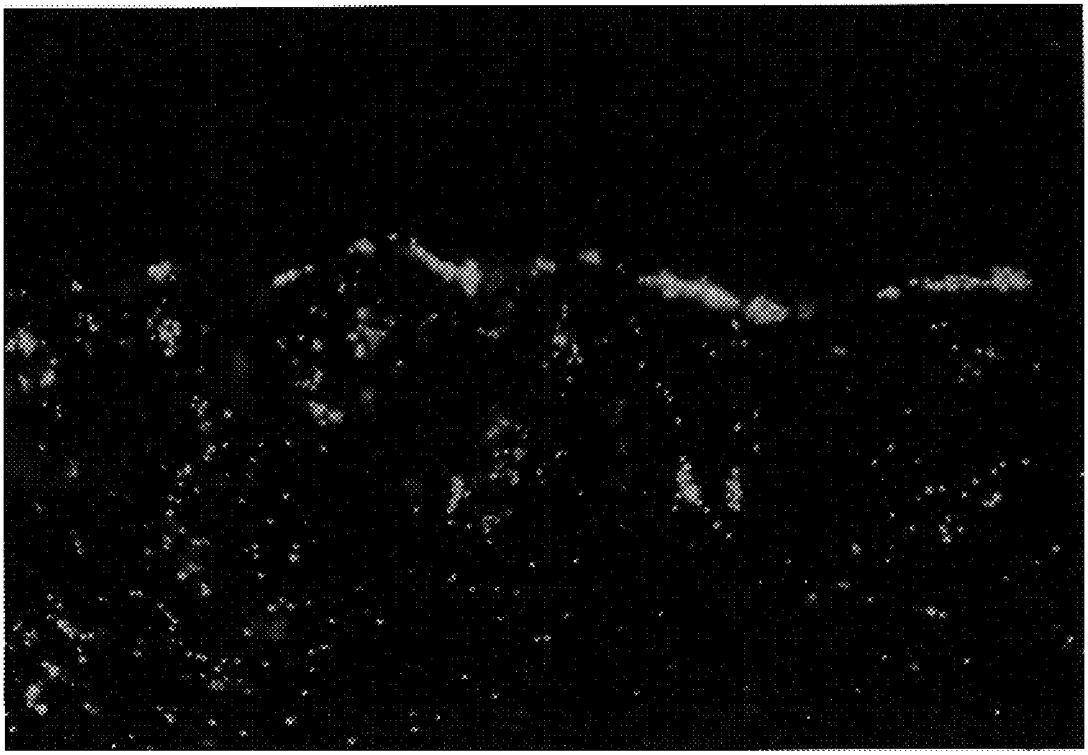

FIG. 17 is an immunofluorescence micrograph of the previously illustrated lymphoid follicle. The fluorescein-labeled microspheres are present mostly in the flank region of the FAE (lower area of the photograph), with declining numbers present in the more apically located regions.

Figure 18:
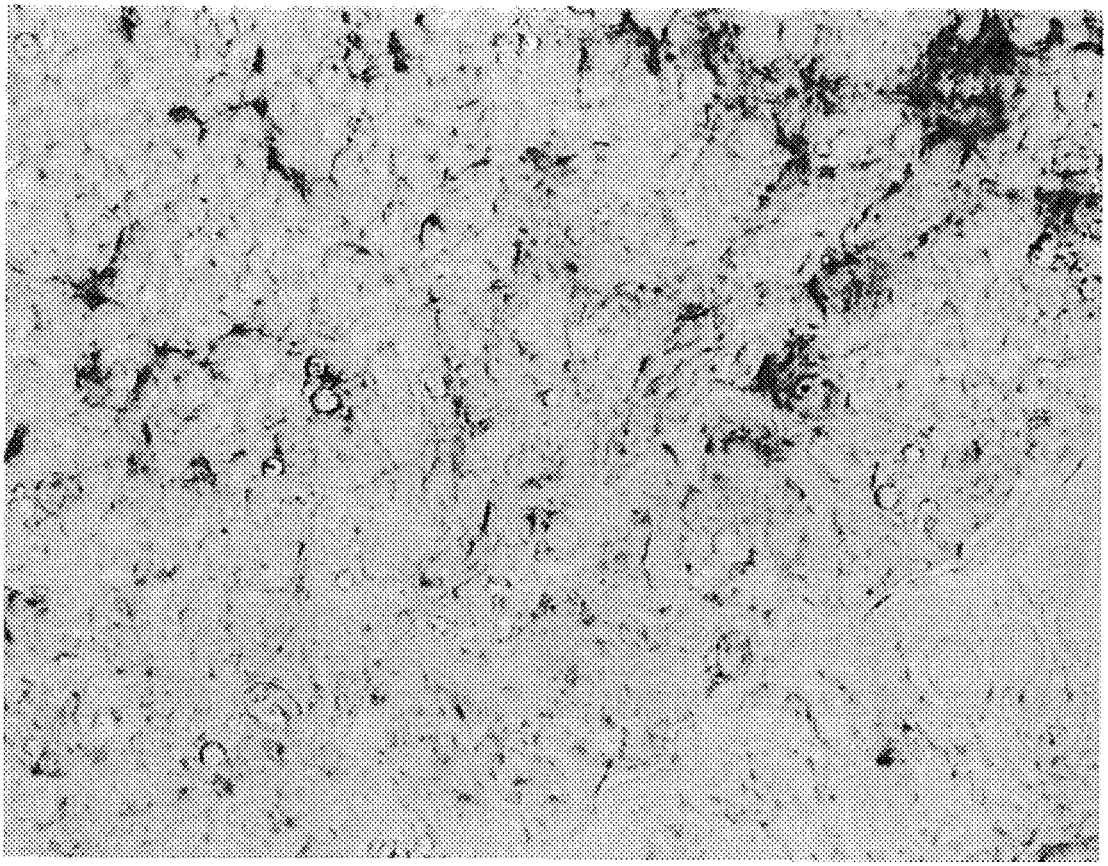

FIG. 18 is a color photograph showing the lymphoid follicle of a Peyer's patch of a New Zealand white rabbit stained for vimentin. The polymerized lactide and glycolide particles appear principally in the FAE area and are practically non-existent in the villous area.

Figure 19:
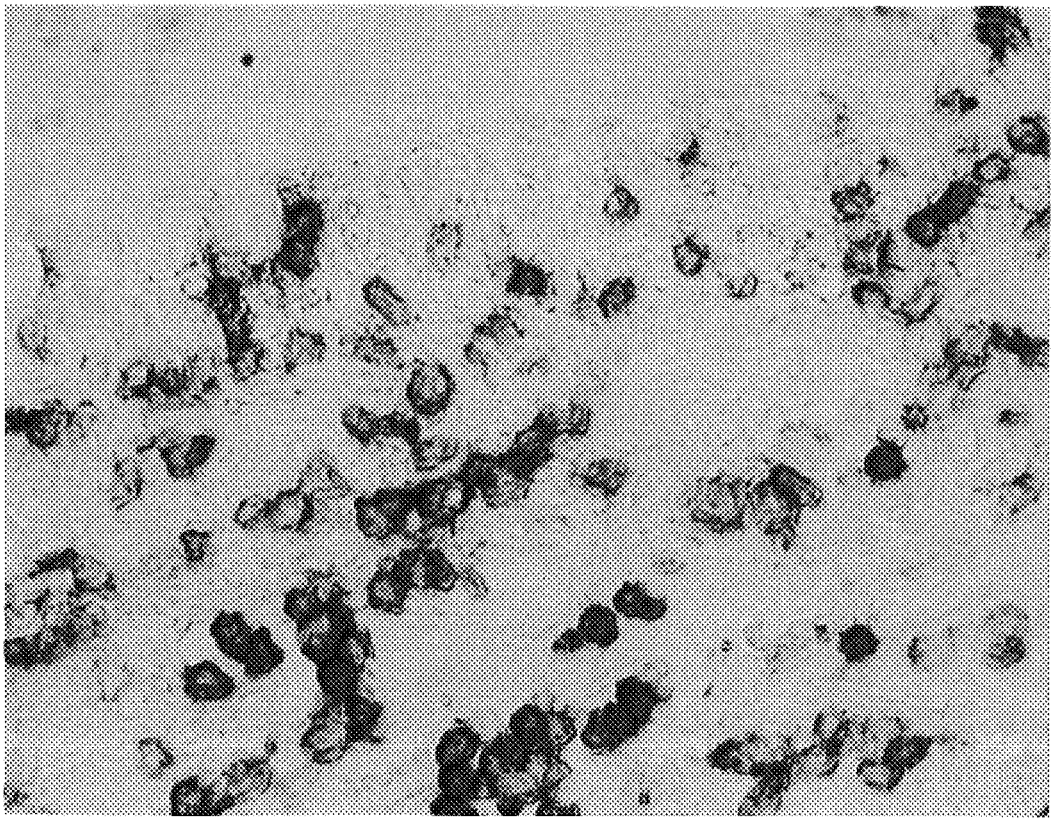

FIG. 19 is a color photograph of the lymphoid follicles of the New Zealand white rabbit's intestines showing the pan-T cell markup stained for CD43. The view shows the villous epithelium, the lamina propria, the location of the copolymer (PLGA) particles and the CD43-positive cells.

VII. DETAILED DESCRIPTION OF THE INVENTION

Use of the emulsion viscosity as the means for controlling the average particle size distribution of polymerized lactide and glycolide microspheres has utility in manufacturing oral and injectable vaccines as well as for use in devices for sustained drug and antibiotic delivery. Preparation of the microspheres was accomplished by a modification of the solvent extraction process to control the sphere size by altering the viscosity of the emulsion either by: 1) predilution of the emulsion oil with an extractant solvent; 2) adding thickening agents such as polybutylene to the emulsion oil to deliberately increase its viscosity; 3) through use of oils with predefined viscosities for preparation of the emulsion; or 4) through deliberately adjusting the viscosity of the paraffin oil by preheating it to a temperature which yields the desired viscosity, taking care that the emulsion time is kept sufficiently short so as to prevent a significant temperature increase during the emulsification process.

It has been found that the oil viscosity is the primary process parameter for controlling the sphere diameter, and that variation in screen and rotor dimensions, emulsification speed and time only exhibit negligible effects on the outcome of the diameter of the microspheres.

The following examples will provide more detailed steps in producing the controlled particle size microspheres of poly (DL-lactide-co-glycolide) by the modified solvent extraction process of the present invention.

EXAMPLE

Solvent Extraction

Preparation of Freeze-Dried Antigen-Sucrose Matrix

Materials 8 ml water 80 mg sucrose 20 mg purified antigen/active

The freeze-drier is turned on and the temperature is set at −25 degrees.

Preparation of the Antigen-Sucrose Matrix

The antigen/active is placed in a 20 ml capacity plastic vial to which water and sucrose are added.

The dispersion is then flash freezed by gently swirling the vial (without the cap) in liquid nitrogen for about one half of an hour.

After about 1000 minutes the temperature is elevated to about +5 degrees for 500 minutes (8.33 hours) and then elevated to about +20 degrees for 1000 minutes (16.67 hours), and the vial is removed.

Preparation of Polymerized Lactide Glycolide (PLG) Solution

The PLG is removed from the freezer and allowed to come to room temperature.

About 2.8 g of acetonitrile is weighed into a 20 ml capacity glass vial and set aside.

After the polymer reaches room temperature, about 1.0 g of the polymer is added to the vial of acetonitrile and a sonicator bath until all of the polymer has dissolved (5–10 minutes).

Homogenization of Sucrose

Preparing the Homogenizer

Homogenization 3.2 g of acetonitrile is weighed in a plastic vial for washings during homogenization.

1.5 g of acetonitrile is weighed into another vial and added to the earlier prepared freeze-dried sucrose-antigen matrix and mixed until it becomes a milky white slurry. The slurry is homogenized at maximum speed for one minute and the 3.2 g of acetonitrile is used to wash the sides of the vial and homogenizer tip, after which the slurry is again homogenized for one minute at maximum speed.

The mixture is separated into two parts by weight by weighing 2.4 g into another 20 ml plastic vial.

The polymer solution prepared earlier is added to one of the vials of homogenized sucrose-antigen and the vial is placed in a sonicator bath for about 2 minutes to ensure proper mixing.

Preparation of Microspheres

The homogenizer is set up with the rotor and fine emulsion screen and the following materials are weighed out: 400 g of light mineral oil in a 600 ml glass beaker and 2500 g of heptane in a 4000 ml propylene beaker. A beaker of heptane is placed under the mixer and a propeller is placed about two-thirds of the way down into the heptane, after which the mixer is started at about 450 rpm.

A Masterflex mode #7550-60 peristaltic pump with pump head model #7518-00 with PharMed tubing, size 16 is set up. The pump speed is set at 300 ml/min after which one end of the tubing is placed into the beaker of heptane.

Approximately 175 ml of the mineral oil is poured into the jacket beaker and the homogenizer head is dipped at 15 degrees into the oil to coat it, after which water is circulated through the beaker.

The polymer/sucrose-antigen solution is poured into the beaker and the vial is rinsed with about 5 ml of mineral oil, and the rinse is added to the beaker.

The homogenizer head is placed into the liquid and then turned to its maximum setting for 3 minutes.

At the end of three minutes the other end of the tubing is placed into the jacketed beaker and the peristaltic pump is started. When the liquid level has dropped to the level of the homogenizer head, the homogenizer is turned off and pumping is continued until all of the liquid has been pumped to the heptane after which the heptane is left stirring for 30 minutes.

Using fresh tubing, the heptane is pumped into centrifuge bottles and centrifuged for 5 minutes at 3000 rpm, 20 degrees celsius. The supernatant is pumped into waste bottles and the sediment is rinsed with heptane (it may be necessary to sonicate the sample for 1 to 5 minutes to break up the sediment).

The supernatant is pumped into the waste bottle and washed with fresh heptane until all the microspheres are in the one tared 50 ml centrifuge tube. This tube is then centrifuged for 5 minutes and washed with fresh heptane three times.

After the final wash and centrifuge cycle, the supernatant is pumped into the waste bottle and the microspheres are air dried with a slow air current for about 5 minutes, and the tube is placed in the vacuum oven at room temperature and left overnight.

The microspheres are removed from the vacuum oven and weighed, after which about 1 mg of the microspheres is put in a 1.5 ml centrifuge tube for evaluation.

Evaluation of Microspheres

About 1 ml of 1% Tween 80 in water is added to the 1 mg of microspheres in the 1.5 ml centrifuge tube, and the tube is sonicated for about 1 minute.

One drop of the dispersion is placed on a glass slide and a coverslip is placed over it. The slide is then placed under a calibrated optical microscope and examined under 100× magnification using a standard oil immersion technique. Using the precalibrated eyepiece micrometer, the diameter of 150 randomly chosen microspheres is determined. (Under 100× magnification, 1 division on the micrometer is equal to 1 micron.)

The numbers are then entered into a Lotus spread sheet program to determine the average size distribution of the particles.

The prior art extraction procedure for production of polylactide; glycolide microencapsulated oral vaccines is based on disbursal of a highly concentrated solution of polymer and acetonitrile into oil, followed by extraction of the acetonitrile and oil with heptane.

The procedure of the invention requires high energy shear to disburse the viscose polymer solution. This high shear process resulted in the generation of major heat change which caused the mineral oil's viscosity to change significantly.

As a result, small increases in shear time or minor differences in the emulsifier's rotor dimensions which increased shear, resulted in increased microsphere diameters, as can be seen from the graph of FIG. 16.

The substitution of stable viscosity machine oils for paraffin oil during the formation of the emulsion resulted in sphere populations whose average sizes and volumes decreased with increasing emulsification times.

This result can be seen in Table I, which is in contrast to the data showing microsphere volume average versus emulsification time and paraffin oil (FIG. 16).

TABLE 1

| | Emulsification Time | | | |
|---|---|---|---|---|
| | 0.75 minutes | | 3.0 minutes | |
| C/S* | V.A.** | D.A.*** | V.A. | D.A. |
| 36 | 2.8 | 0.9 | 2.4 | 0.9 |
| 50 | 7.3 | 2.9 | 6.8 | 3.2 |
| 65 | 7.9 | 3.3 | 6.9 | 2.9 |
| 72 | 4.9 | 1.0 | 3.0 | 0.9 |
| 80 | 2.4 | 1.1 | 1.4 | 0.9 |

* = Centistokes
** = Volume Average
*** = Diameter Average

Both paraffin emulsions and machine oil emulsions underwent similar temperature increases during the emulsion process, and the differences between these two oils appears to be due to maintenance of a relatively constant emulsion viscosity by the machine oils. At a constant viscosity, increased homogenization time appears to have resulted in a progressively finer dispersal of the polymer-acetonitrile solution into the oil. Viscosity breakdown in the paraffin oil appears to have allowed particles to recoalesce as the emulsion temperature increased.

Reducing the viscosity of the paraffin oil by diluting it with either heptane or iso-octane resulted in the formation of a progressively larger spheres as can be seen in Table 2.

TABLE 2

| Sphere Diameters Resulting From Dilution of the Emulsion Oil | | | |
|---|---|---|---|
| Solvent/ | Diameter Averages in U | | |
| Oil Mixture | H* | 10** | 10*** |
| 1/2 | 11.0 | 4.6 | 9.7 |
| 1/4 | 2.6 | 5.0 | 3.3 |
| 1/8 | 1.5 | 2.2 | 2.6 |
| 1/16 | 1.2 | 1.4 | 0.6 |
| No Solvent | 1.0 | 1.0 | 0.6 |

* = Heptane Diluent,
** = Iso-octane,
*** = 2nd Series of Iso-octane Batches Employing Reduced Shear Forces The results of these tables show that sphere size can be controlled by altering the viscosity of the emulsion oil through its pre-dilution with an extractant solvent, provided that the emulsion time is kept sufficiently short so as to prevent a significant temperature increase during the emulsification process.

The data in Table 1 shows a relationship between the microsphere size and oil viscosity in that, microsphere size increased as oil viscosity increased from 36 to 65 centistokes and then decreased from 65 to 80 centistokes, which appears to indicate a bell-shaped sphere size distribution as viscosity increased.

FIG. 17 shows viscosity versus sphere diameter obtained with paraffin oil diluted with iso-octane.

FIG. 18 shows viscosity versus sphere diameter obtained with paraffin oil diluted with heptane.

FIG. 19 shows viscosity versus sphere diameter obtained with machine oils.

A histochemical and immunohistochemical analysis of the uptake of PLG and polystyrene microparticles by Peyer's patches from a New Zealand white rabbit was conducted using the poly (DL-lactide-co-glycolide) copolymer in which the molar parts of polymerized lactide and glycolide were 50:50, as prepared according to the modified solvent extraction process of the invention.

Fluorescent polystyrene microspheres were also used as a comparison to test these microparticles as carriers of immunogens for oral immunization, and to ascertain or determine the actual location of their uptake by gut lymphoid tissues, and to ascertain which tissues were engaged in the uptake.

The study also served in part to ascertain if encapsulation may protect the antigens from proteolytic degradation in the gut lumen and facilitate their uptake and retention in the intestinal lymphoid tissues, as a thorough understanding of the fate of ingested antigen-containing microparticles is important in using antigens which have been microencapsulated for enteric immunization strategies.

VIII. METHOD

Fluorescent polystyrene microspheres and unlabelled poly (lactide-co-glycolide) microspheres of diameters of 0.5, 1, and 2 um where instilled into the lumens of in situ rabbit intestinal loops.

After a period of between about 1 to 2 hours, the loops were removed, and sections were cut and reacted histochemically for acid (AcP), phosphatase and immunohistochemically in a biotin-streptavidin method with several monoclonal antibodies to the rabbit lymphoid cell antigens.

The rabbits were anesthetized New Zealand white rabbits and the dimensions of the intestinal loops were 2 cm (containing Peyer's patches) and the tissue blocks were excised and fixed in periodate-lysine-praformaldehyde.

The results of these tests show that both kinds of particles (0.5>1>2 μm were taken up by the Peyer's patches.

However, the particles of copolymer from the invention process principally taken up in the Peyer's patch region have a volume average of about 1.0 to about 7.0 micrometers as the particle size distribution.

Particles of copolymer from the invention process principally taken up in the villous epithelium of the intestines have a volume average of from about 0.5 to about 2.0 micrometers.

Tables 3 and 4 show respectively, the particles used when testing placement in Peyer's patch and villous regions.

TABLE 3

Microspheres: Particle Size Distribution by Microscopy

Stage magnification: 100 ×

Calibration: 1 div = (u) 1.00

| Reading | Dia., | u | d | 3 | FD | 3 | Dist | .01*f*d | F*D | Dist. |
|---|---|---|---|---|---|---|---|---|---|---|
| | Frequency | | | | | | % Vol. | | | % Num |
| 1 | 40 | 1 | 1 | | 40 | | 0 | 0 | 40 | 27 |
| 2 | 41 | 2 | 8 | | 329 | | 3 | 0 | 82 | 27 |
| 3 | 25 | 3 | 27 | | 675 | | 6 | 2 | 75 | 17 |
| 4 | 13 | 4 | 64 | | 832 | | 7 | 4 | 52 | 9 |
| 5 | 11 | 5 | 125 | | 1375 | | 11 | 14 | 55 | 7 |
| 6 | 9 | 6 | 216 | | 1944 | | 16 | 35 | 54 | 6 |
| 7 | 5 | 7 | 343 | | 1715 | | 14 | 48 | 35 | 3 |
| 8 | 1 | 8 | 512 | | 512 | | 4 | 22 | 8 | 1 |
| 9 | 1 | 9 | 729 | | 729 | | 6 | 44 | 9 | 1 |
| 10 | 4 | 10 | 1000 | | 4000 | | 33 | 329 | 40 | 3 |
| Total | 150 | 55 | 3025 | | 12150 | | 85 | 498 | 450 | 100 |
| average | | 5.50 | 6.71 | | | | 2.15 | | 3 | 2.15 |
| S.D. | | 2.87 | 6.88 | | | | 2.08 | | 2.85 | 2.12 |

| | between or equal to 5-10 u | |
|---|---|---|
| | % volume | % number |
| | 73.25 | 13.53 |
| | greater than 10 u | |
| | % volume | % number |
| | 0.00 | 0.00 |
| | between or equal to 1-5 u | |
| | % volume | % number |
| | 26.75 | 86.67 |

Particle Size Distribution

| | |
|---|---|
| Volume Average (u) | 7.9 |
| Number Average (u) | 3.0 |

AGGREGATION DATA

| | | |
|---|---|---|
| Vol % Aggregated | 0.00 | Weight % |
| Number % Aggregated | 0.00 | number % |
| Avg Part Size Aggregated | ERR | |
| Avg # of Part per Aggregate | ERR | |

TABLE 4

Microspheres: Particle Size Distribution by Microscopy

Stage magnification: 100 ×

Calibration: 1 div = (u) 1.00

| Reading | Dia., | u | d | 3 | F*D | 3 | Dist | .01*f*d | F*D | Dist. |
|---|---|---|---|---|---|---|---|---|---|---|
| | Frequency | | | | | | % Vol. | | | % Num |
| 1 | 103 | 1 | 1 | | 103 | | 3 | 0 | 103 | 69 |
| 2 | 17 | 2 | 8 | | 136 | | 4 | 0 | 34 | 11 |
| 3 | 16 | 3 | 27 | | 432 | | 12 | 3 | 48 | 11 |
| 4 | 2 | 4 | 64 | | 128 | | 4 | 2 | 8 | 1 |
| 5 | 5 | 5 | 125 | | 625 | | 18 | 22 | 25 | 3 |
| 6 | 2 | 6 | 216 | | 432 | | 12 | 26 | 12 | 1 |
| 7 | 5 | 7 | 343 | | 1715 | | 48 | 165 | 35 | 3 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| 0 | 0 | 0 | 0 | | 0 | | 0 | 0 | 0 | 0 |
| Total | 150 | 28 | 3025 | | 3571 | | 100 | 219 | 265 | 100 |
| average | | 1.56 | 6.71 | | | | 1.77 | | 2 | 1.77 |
| S.D. | | 2.31 | 6.88 | | | | 2.26 | | 2.96 | 2.50 |

| | between or equal to 5-10 u | |
|---|---|---|
| | % volume | % number |
| | 60.12 | 4.67 |
| | greater than 10 u | |
| | % volume | % number |
| | 0.00 | 0.00 |
| | between or equal to 1-5 u | |
| | % volume | % number |
| | 39.88 | 95.33 |

Particle Size Distribution

| | |
|---|---|
| Volume Average (u) | 6.0 |
| Number Average (u) | 1.8 |

AGGREGATION DATA

| | |
|---|---|
| Vol % Aggregated | 0.00 |
| Number % Aggregated | 0.00 |
| Avg Part Size Aggregated | ERR |
| Avg # of Part per Aggregate | ERR |

The significance of what particle size distribution of the copolymer prepared according to the invention process is taken up in the villous epithelium section of the intestine is that, for oral administration of a vaccine (especially when no booster vaccine is administered), the antigen must principally be uptaken by the villous epithelium region, which is more than 90% of the area of the intestine needed for effective immunization. On the other hand, the fact that some of the smaller particle size distribution copolymer materials are also taken up by the Peyer's patch region of the intestine while the majority of the copolymer is taken up by the villous epithelium section indicates that several combinations of modes of immunization may be effected through vaccine.

The following information obtains from a immunohistochemistry basis:

IMMUNOHISTOCHEMISTRY

Antibodies

IMMUNOHISTOCHEMISTRY

| Antibodies: Monoclonal Antibody | Source | Antigen Recognized |
|---|---|---|
| V9 | Biomeda | Vimentin (M cell marker) |
| L11-35 | Serotec | CD43 (pan T cell) |
| 45-3 | Spring Valley | MHC11 |
| Ken-4 | Spring Valley | CD4 |
| 12C7 | Spring Valley | CD8 |
| NRBM | Serotec | Ig u chain |
| Procedure: | | |
| Biotin-streptavin method | | |

Uptake was greatest along the flanks of the follicles, where M cells (demonstrated by anti-vimentin MAb) were most numerous. While the particles were sometimes present within M cell cytoplasm, they were much more numerous in the lymphocyte pockets of the M cells.

In the pockets, the particles were intermingled with cells that were CD43+, CD8−, CD4−, Igu−, and MHC II+.

The results showed that, occasionally, the particles were present within large AcP+ cells in the pockets. In the follicular tissue beneath the M cell-rich epithelium, particles were very numerous in the vicinity of MHC II+ cells and occasionally within the large AcP+ cells.

Unexpectedly, microspheres also entered non-M cell epithelium cells, especially in the domes. These cells were vimentin negative AcP+. Microparticles were sparse or absent in the subepithelial tissue beneath the cells.

As a result of these tests, it became clear that both M cells and non-M cells in the rabbit PP follicle-associated epithelium can take up certain microparticles. Only the M cells may be capable of permitting migration of the particles to adjacent cells.

Microparticles taken up by the M cells appear to migrate to lymphocyte pockets richly populated with MHC II+ cells and CD8−/CD4− T cells, as well as to a certain extent to AcP+ phagocytic cells.

What is claimed is:

1. In a solvent extraction process for preparing microspheres of an antigen containing biodegradable poly(DL-lactide-co-glycolide), the improvement comprising:

preparing a lyophilized antigen-sucrose matrix; adding acetonitrile solvent to the antigen-sucrose matrix to form a solution;

preparing a solution of a biodegradable poly (DL-lactide-co-glycolide) polymer by adding acetonitrile solvent to the polymer;

adding the biodegradable poly (DL-lactide-co-glycolide) polymer acetonitrile solution to the antigen-sucrose acetonitrile solution;

adding an oil to the poly (DL-lactide-co-glycolide) polymer-sucrose-antigen solution to form an emulsion having a controlled viscosity, that corresponds to a predetermined average particle size of distributions of microspheres of poly (DL-lactide-co-glycolide) biodegradable polymers of from about 0.5 to about 7.0 micrometers;

centrifuging the emulsion of controlled viscosity and removing a supernatant to obtain microspheres of the predetermined range of particle size distributions.

2. The process of claim 1, wherein the oil is selected with a predefined viscosity to form the microspheres.

3. The process of claim 1, wherein a thickening agent is added to the oil to increase its viscosity.

4. The process of claim 1, wherein the oil is prediluted with an extractant solvent.

5. The process of claim 1, wherein the oil is a paraffin oil in which the viscosity is adjusted by preheating to a temperature of desired viscosity.

6. The process of claim 1, wherein relative ratios between the lactide and glycolide is 50:50.

7. The process of claim 1, wherein the average particle size distribution is from about 1.0 to about 2.0 micrometers.

*8. The process of claim 1, wherein the oil is a paraffin oil.*

*9. The process of claim 8, wherein the viscosity of the paraffin oil is reduced by diluting it with heptane or isooctane.*

*10. The process of claim 2, wherein the viscosity of the oil is reduced to produce larger spheres.*

*11. The process of claim 3, wherein the thickening agent is polybutylene.*

*12. A method of controlling average particle size of microspheres containing an agent in a solvent extraction process, comprising:*

*adjusting a viscosity of an oil to a value that corresponds to a predetermined average particle size of microspheres to control said size of said microspheres;*

*adding said oil to a biodegradable poly(DL-lactide-co-glycolide) polymer-stabilizer agent solution emulsion;*

*centrifuging the emulsion;*

*and removing said microspheres of said predetermined average particle size.*

* * * * *